(12) United States Patent
Kane (10) Patent No.: US 8,342,034 B2
(45) Date of Patent: Jan. 1, 2013

(54) SYSTEM AND METHOD TO TEST SPECIMENS

(75) Inventor: Daniel J. Kane, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 300 days.

(21) Appl. No.: 12/631,659

(22) Filed: Dec. 4, 2009

(65) Prior Publication Data
US 2011/0132100 A1 Jun. 9, 2011

(51) Int. Cl.
*G01N 3/08* (2006.01)
(52) U.S. Cl. .......................................... 73/826
(58) Field of Classification Search .............. 73/826
See application file for complete search history.

(56) References Cited

U.S. PATENT DOCUMENTS

| | | | |
|---|---|---|---|
| 4,047,425 A * | 9/1977 | Handy et al. ............. | 73/822 |
| 4,358,961 A | 11/1982 | Woods | |
| 7,051,597 B2 | 5/2006 | Greszczuk | |

OTHER PUBLICATIONS

Horide, Akihiro, et al., Characterization of Fracture Process During Ring Burst Test of FW-FRP Composites with Damage, Advanced Composite Materials, vol. 8, No. 2, pp. 139-151 (1999).
European Search Report mailed Mar. 11, 2011.

\* cited by examiner

*Primary Examiner* — Lisa Caputo
*Assistant Examiner* — Octavia Davis-Hollington
(74) *Attorney, Agent, or Firm* — Caven & Aghevli LLC (57) ABSTRACT

An apparatus and method to test a specimen is disclosed. In one embodiment, the apparatus comprises a housing defining a passage having a length extending along a longitudinal axis, an anvil movable in the passage between a first position and a second position along the longitudinal axis, the anvil comprising a tapered shaft section, an expandable mandrel having an inner surface adapted to fit around a portion of the tapered shaft section and an outer surface adapted to receive a test specimen, and a first block to limit motion of the mandrel. In use, moving the anvil between the first position and the second position causes the mandrel to expand in a circumferential direction, thereby applying a circumferential tension force to the specimen.

16 Claims, 6 Drawing Sheets

SYSTEM AND METHOD TO TEST SPECIMENS

FIELD OF THE DISCLOSURE

This invention relates to destructive testing, and more particularly to apparatus and method for circumferential tension testing annular components.

BACKGROUND

Various applications require components which operate under circumferential tension stress in a circumferential direction. By way of example, many fasteners operate under at least a component of circumferential tension. Failure of such fasteners can be expensive to repair and can cause delays in manufacturing and design. Thus, systems and methods to test specimens which operate under circumferential tension may find utility.

SUMMARY

In various aspects, apparatus and methods to test specimens in circumferential tension are provided. In some embodiments, a specimen is mounted on an expandable mandrel, which is in turn mounted on an anvil having a tapered shaft. The anvil is positioned in a passage of a housing such that the mandrel and the specimen are blocked from motion. A load is applied to the anvil, enabling the tapered shaft to move relative to the mandrel, thereby expanding the mandrel and placing the specimen under circumferential tension. The anvil may be loaded until the specimen fails. Data relating to the force applied to the anvil and the displacement of the anvil may be collected and analyzed to determine the relative strength, ductility, and stiffness for the specimen.

Thus, in one aspect there is provided an apparatus to test a specimen. In one embodiment, the apparatus comprises a housing defining a passage having a length extending along a longitudinal axis, an anvil movable in the passage between a first position and a second position along the longitudinal axis, the anvil comprising a tapered shaft section, an expandable mandrel having an inner surface adapted to fit around a portion of the tapered shaft section and an outer surface adapted to receive a test specimen, and a first block to limit motion of the mandrel. In use, moving the anvil between the first position and the second position causes the mandrel to expand in a circumferential direction, thereby applying a circumferential tension force to the specimen.

In another aspect there is provided a method to test a specimen. In one embodiment, the method comprises providing a housing defining a passage having a length extending along a longitudinal axis, mounting the specimen on the outer surface of an expandable mandrel, mounting the expandable mandrel on a tapered shaft section of an anvil, positioning the anvil in the passage having a length extending along a longitudinal axis, moving the anvil in the shaft between a first position and a second position along the longitudinal axis, and limiting the motion of the mandrel in the shaft, such that moving the anvil between the first position and the second position causes the mandrel to expand, thereby applying a circumferential tension force to the specimen.

The features, functions and advantages discussed herein can be achieved independently in various embodiments described herein or may be combined in yet other embodiments, further details of which can be seen with reference to the following description and drawings.

BRIEF DESCRIPTION OF THE DRAWINGS

The detailed description is described with reference to the accompanying figures.

DETAILED DESCRIPTION

Described herein are exemplary systems and methods to test specimens. In the following description, numerous specific details are set forth to provide a thorough understanding of various embodiments. However, it will be understood by those skilled in the art that the various embodiments may be practiced without the specific details. In other instances, well-known methods, procedures, components, and circuits have not been illustrated or described in detail so as not to obscure the particular embodiments.

Figure 1:
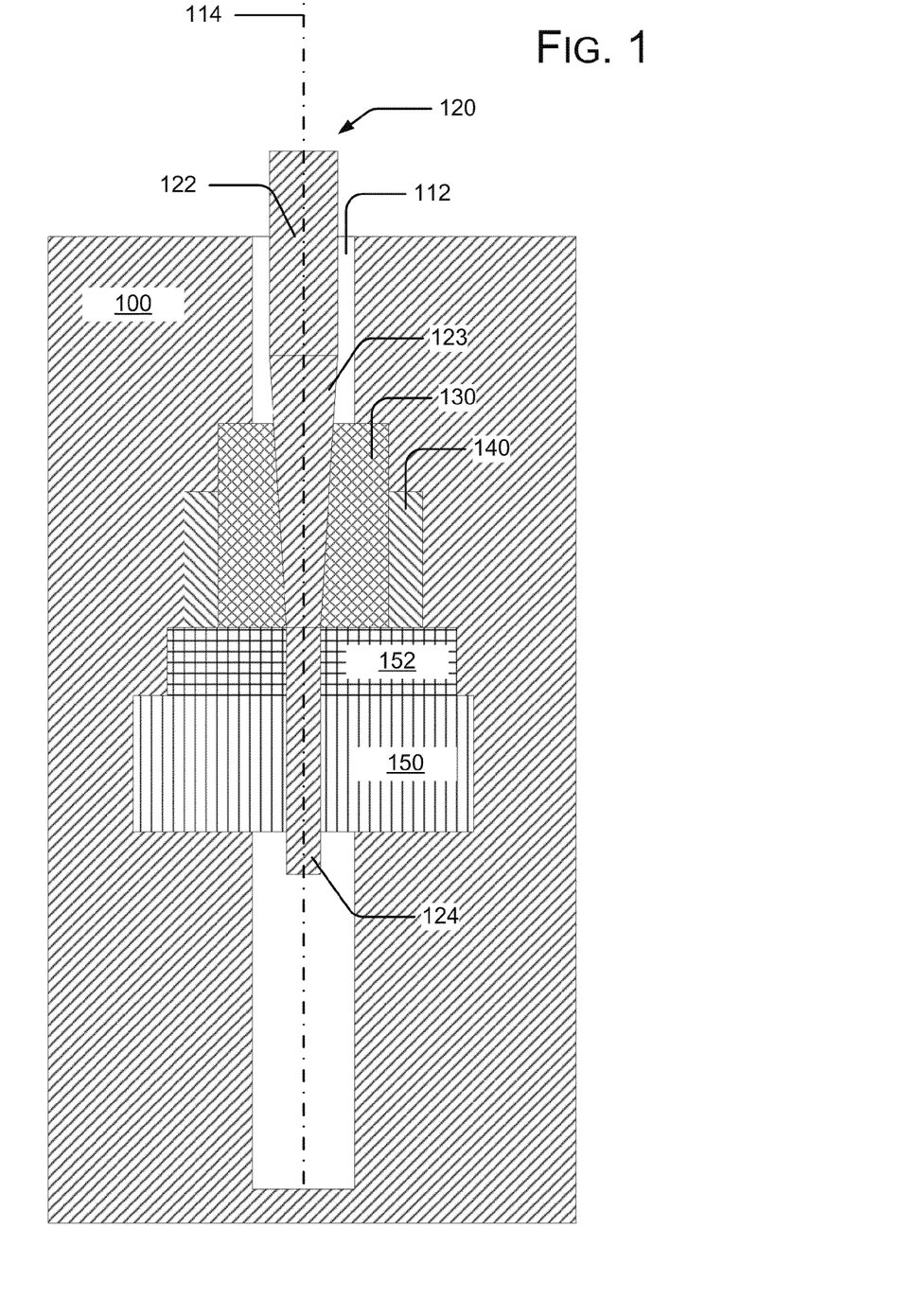
FIG. 1 is a cross-sectional schematic illustration of a portion of a system to test specimens in accordance with some embodiments.
Figure 2:
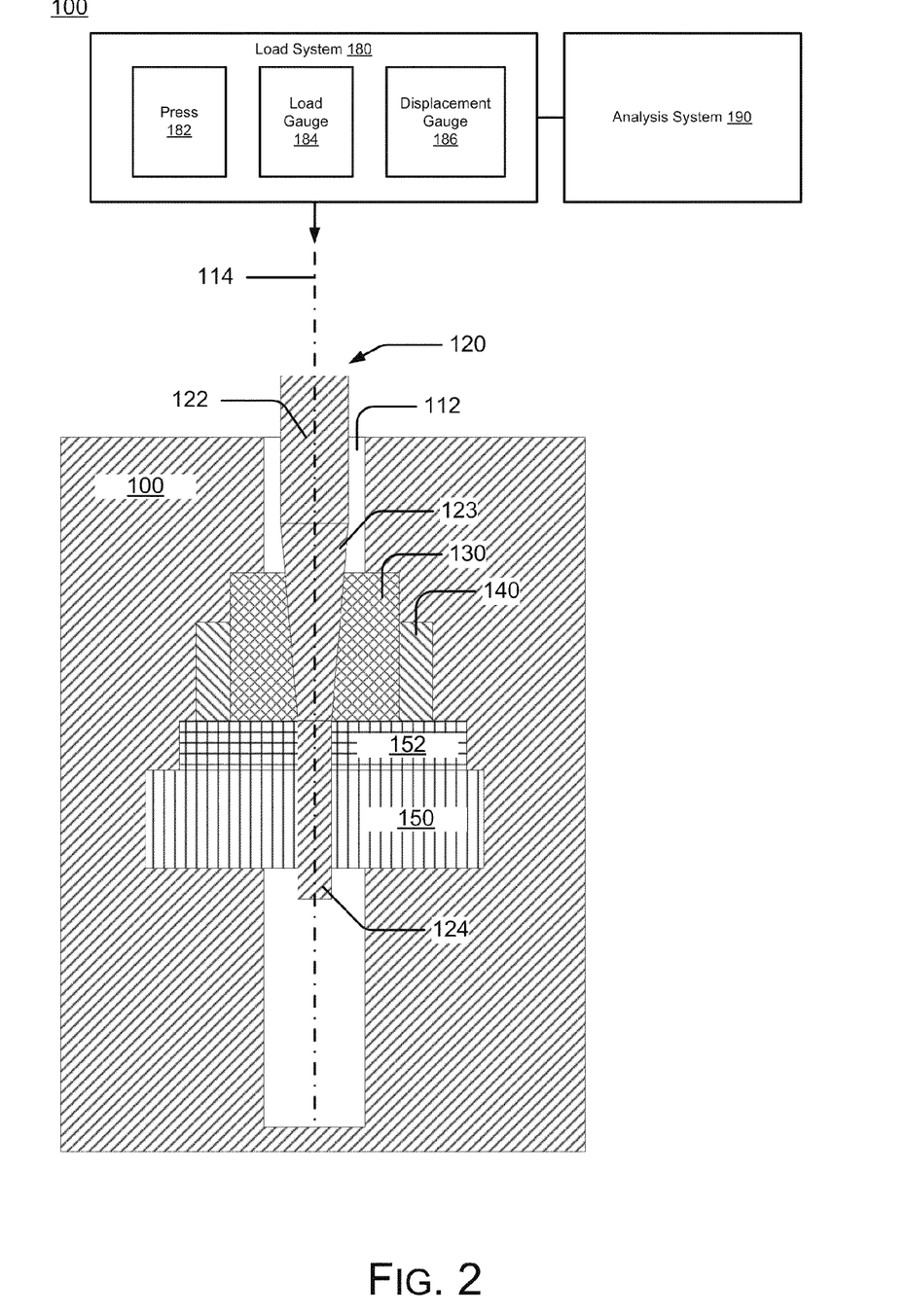
FIG. 2 is a schematic illustration of a system to test specimens in accordance with some embodiments.

FIG. 1 is a cross-sectional schematic illustration of a system to test specimens in accordance with some embodiments, and FIG. 2 is a schematic illustration of a system 100 to test specimens in accordance with some embodiments. Referring to FIGS. 1-2, the system comprises a housing 110 which defines a passage 112 having a length extending along a longitudinal axis 114. As illustrated in FIG. 2, in some embodiments housing 110 comprises a work area 116 defined as an aperture in the housing. The work area 116 enables a user of the system to access components of the system when the system is in use.

As shown in both FIG. 1 and FIG. 2, the system 100 further comprises an anvil 120 which is movable in the passage between a first position and a second position along the longitudinal axis 114. In the embodiment depicted in FIG. 1 and FIG. 2, the anvil 120 comprises a first section 122 which is substantially cylindrical, a second tapered section 123 which decreases in diameter along its longitudinal extent, and a third section 124 that is substantially cylindrical. Thus, the tapered section 123 of shaft 122 has a first diameter at a proximal end adjacent the head 124 and a second diameter, less than the first diameter, at a distal end.

Figure 3A:
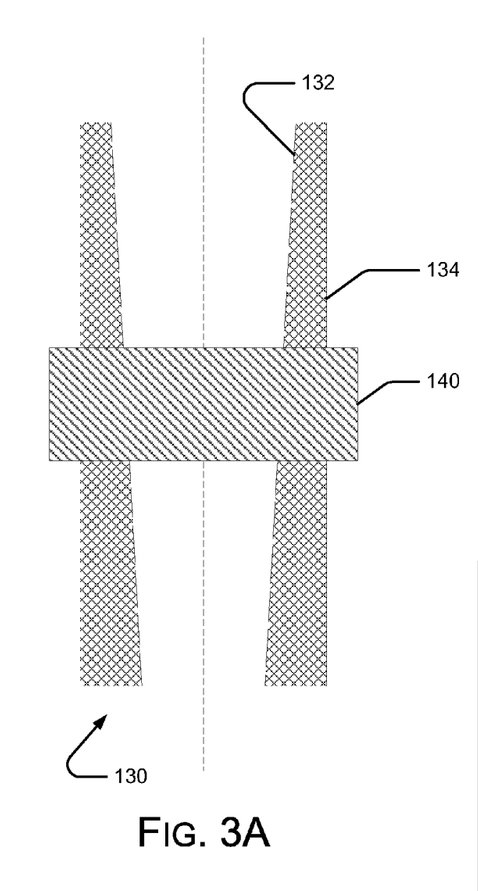
FIG. 3A is a cross-sectional schematic illustration of a mandrel for use in a system to test specimens in accordance with some embodiments.
Figure 3B:
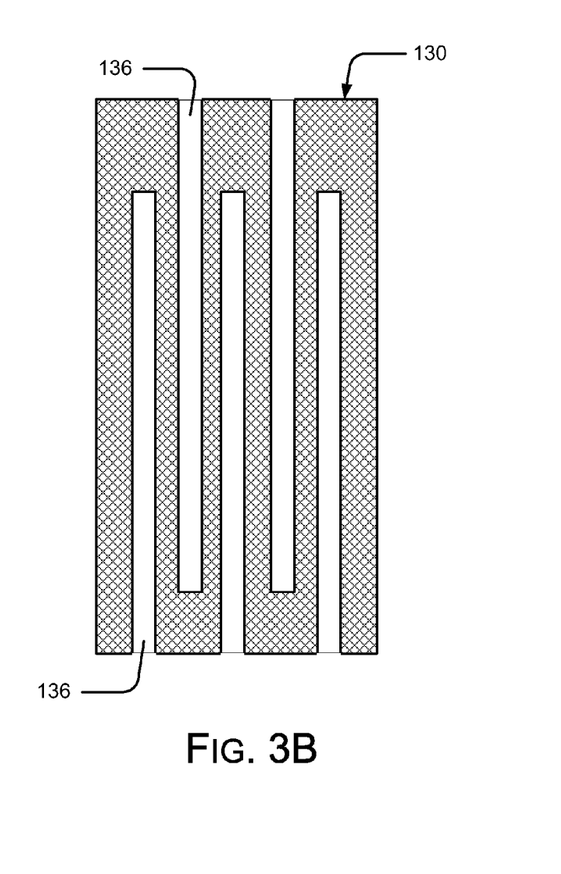
FIG. 3B is a plan view of a section of a mandrel for use in a system to test specimens in accordance with some embodiments.

Referring now to FIGS. 3A and 3B, mandrel 130 has an inner surface 132 adapted to fit around a portion of the tapered shaft and an outer surface 134 adapted to receive a test specimen 140. The mandrel 130 is adapted to such that it can expand in a circumferential direction. For example, in the embodiment depicted in plan view in FIG. 3B the mandrel 130 comprises a plurality of slots 136 formed along the longitudinal axis of the mandrel 130 such that the mandrel 130 is expandable in a circumferential direction when the mandrel 130 is wrapped around a shaft. Referring again to FIG. 3A, in one embodiment the mandrel comprises an inner surface 132 and an outer surface 134 and varies in thickness along a longitudinal axis, such that the inner surface 132 of the mandrel 130 follows a surface of the tapered section 123 of shaft 122 while the outer surface 134 of the mandrel 130 maintains a substantially constant radius.

Referring back to FIG. 1 and FIG. 2, the anvil 120 with the mandrel 130 and test specimen 140 are positioned within the passage 112 of the housing such that the lower surface of the mandrel 130 rests against a block 150, which limits the motion of the mandrel 130 in the passage 112. In some embodiments the block 150 may be separate from the housing 110. In other embodiments the block 150 may be an integral part of the housing 110. In some embodiments a second block 152 may be used to limit the motion of the specimen 140 during a set-up process. In some embodiments the specimen 140 may be held in place by the circumferential pressure applied by the mandrel 130. In such embodiments the block 152 would not be necessary. Referring to FIG. 2, In some embodiments the block 152 may be removed during the testing process.

The particular dimensions of the various system components are not critical, and are primarily a function of the size of the specimen 140 being tested. In some embodiments, the housing 110 measures between 2.0 inches and 10.0 inches in height, 2.0 inches and 6.0 inches in width, and 1.0 inches and 4.0 inches in depth. The anvil 120 measures between 1.0 inches and 8.0 inches in length, and the shaft measures between 0.5 inches and 2.0 inches in length, and the diameter of the tapered section 123 of shaft 122 reduces from tapers in a range of approximately 0.5 degrees to 10.0 degrees. The mandrel measures between 0.5 inches and 6.0 inches in length.

The particular materials from which the various components are formed are not critical, and are in part a function of the forces which need to be translated by the system 100. In some embodiments the housing 110, anvil 120, mandrel 130, and blocks 150, 152 may be formed from a suitable metal, e.g., steel, aluminum, or the like.

Referring back to FIG. 2, the system 100 may comprise, or be coupled to, a load system 180 to apply a load to the anvil 120. It may also be coupled to an analysis system 190 to analyze data from the load system 180. The load system 180 and the analysis system 190 may be separate from the housing 110. In some embodiments, load system 180 comprises a press 182, one or more load gauges 184, and one or more displacement gauges 186. Press 182 may be implemented as a mechanical press, a hydraulic press, a pneumatic press, or any press capable of generating sufficient force to load the anvil 120. Load gauge 184 may be implemented as a strain gauge or any gauge capable of measuring the load which the press 182 applies to the anvil 120. Displacement gauge 186 may be implemented as a laser-based displacement gauge, a capacitance sensor, or any other gauge capable of measuring displacement of the anvil 120 when a load is applied to the anvil 120.

Analysis system 190 collects data from the load gauge and displacement gauge 186 and analyzes the data to determine one or more stress failure characteristics of the specimen. In some embodiments aspects of analysis system 190 may be embodied as logic instructions which execute on a general purpose computing device, e.g., a desktop computer, a laptop computer or the like. In alternate embodiments the analysis system may be implemented as in a programmable logic device (e.g., a field programmable gate array) or may be reduced to hardwired circuitry in a dedicated logic device (e.g., an application specific integrated circuit).

Figure 4:
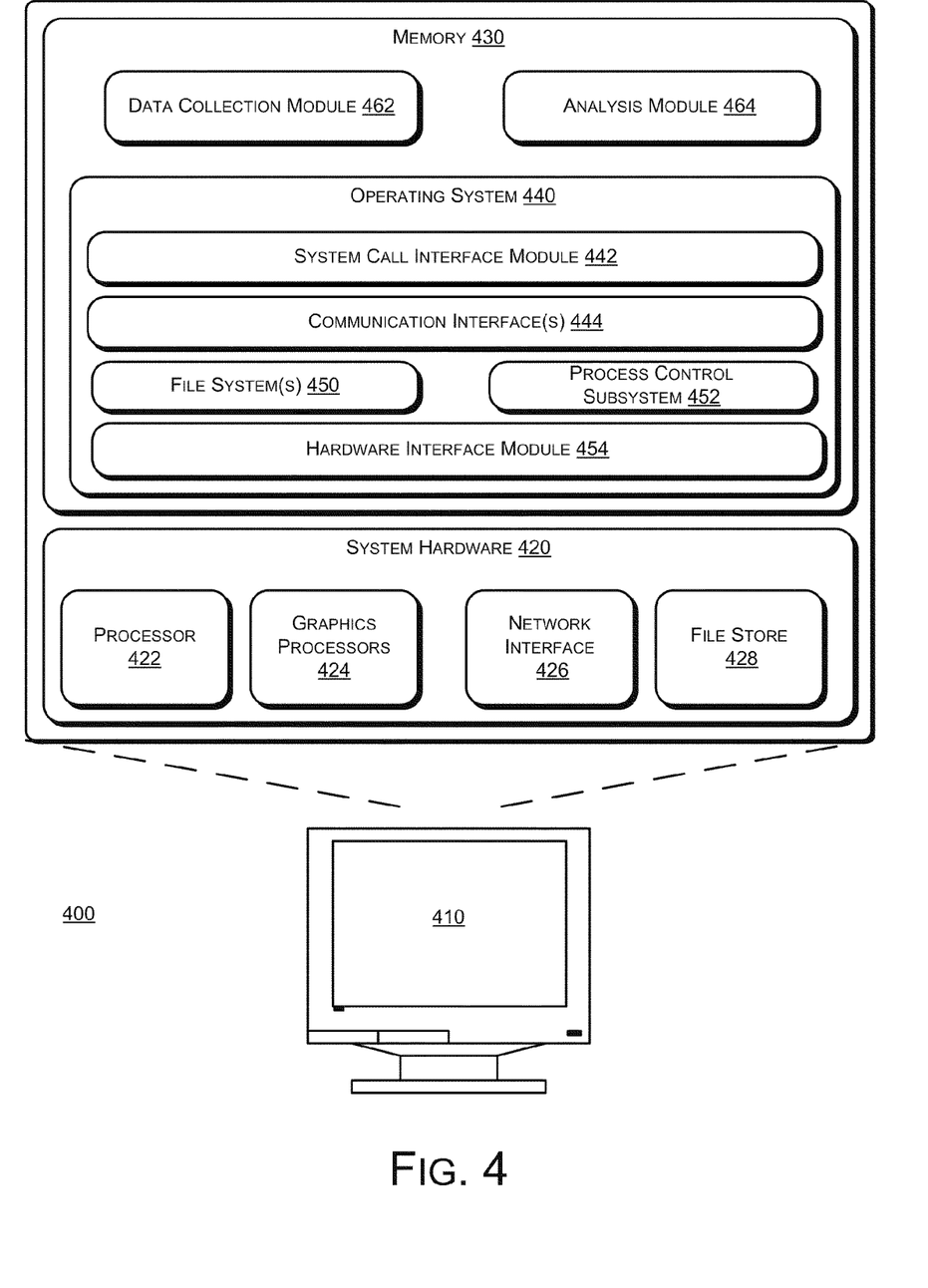
FIG. 4 is a schematic illustration of a computing system in which portions of a system for wire detection may be implemented according to embodiments.

FIG. 4 is a schematic illustration of a computing system in which portions of an analysis system may be implemented, according to embodiments. In some embodiments, a data collection module 462 and an analysis module 464 may be implemented as logic instructions which execute on a general purpose processor, e.g., a computing device. In one embodiment, system 400 includes system hardware 420 and memory 430, which may be implemented as random access memory and/or read-only memory.

System hardware 420 may include one or more processors 422, a graphics processor 424, network interfaces 426, and a file store 428. As used herein, the term "processor" should be construed to include any type of computational element, such as but not limited to, a microprocessor, a microcontroller, a complex instruction set computing (CISC) microprocessor, a reduced instruction set (RISC) microprocessor, a very long instruction word (VLIW) microprocessor, or any other type of processor or processing circuit.

Graphics processor 424 may function as adjunct processor that manages graphics and/or video operations. Graphics processors 424 may be integrated onto a motherboard of the processing device 400 or may be coupled via an expansion slot on a motherboard.

In one embodiment, network interface 426 may be a wired interface such as an Ethernet interface or a wireless interface such as an IEEE 802.11a, b or g-compliant interface. Another example of a wireless interface would be a general packet radio service (GPRS) interface.

A file store 428 which may be implemented as, e.g., non-volatile memory, one or more hard drives, CD-ROM drives, DVD-ROM drives, or other types of storage devices. File store 428 may also be external to system 400 such as, e.g., one or more external hard drives, network attached storage, or a separate storage network.

System 400 may include, or be coupled to, a display device 410. In some embodiments, display device 410 may comprise a liquid crystal display (LCD) device, a cathode ray tube (CRT) device, or the like. Display 410 may comprise, or be coupled to, one or more auditory interfaces, e.g., a speaker.

Memory 430 may include an operating system 440 for managing operations of system 400. In one embodiment, operating system 440 includes a hardware interface module 454 that provides an interface to system hardware 220. In addition, operating system 440 may include a file system 450 that manages files used in the operation of system 400 and a process control subsystem 452 that manages processes executing on system 400.

Operating system 440 may include (or manage) one or more communication interfaces that may operate in conjunction with system hardware 420 to receive data packets and/or data streams from a remote source. Operating system 440 may further include a system call interface module 442 that provides an interface between the operating system 440 and one or more application modules resident in memory 430. Operating system 440 may be embodied as a UNIX operating system or any derivative thereof (e.g., Linux, Solaris, etc.) or as a Windows® brand operating system, or other operating systems.

In one embodiment, memory 430 includes a data collection module 462 to collect data from the load gauge 184 and the displacement gauge 186 and an analysis module 464 to analyze the data to determine at least one stress characteristic of a signal transmitted from the reflected radiation collecting assembly 110. In one embodiment, analysis module 464 may include logic instructions encoded in a computer-readable storage medium which, when executed by processor 422, cause the processor 422 to analyze data collected from the load gauge and the displacement gauge and to determine one or more stress characteristics of the specimen from the data.

Figure 5:
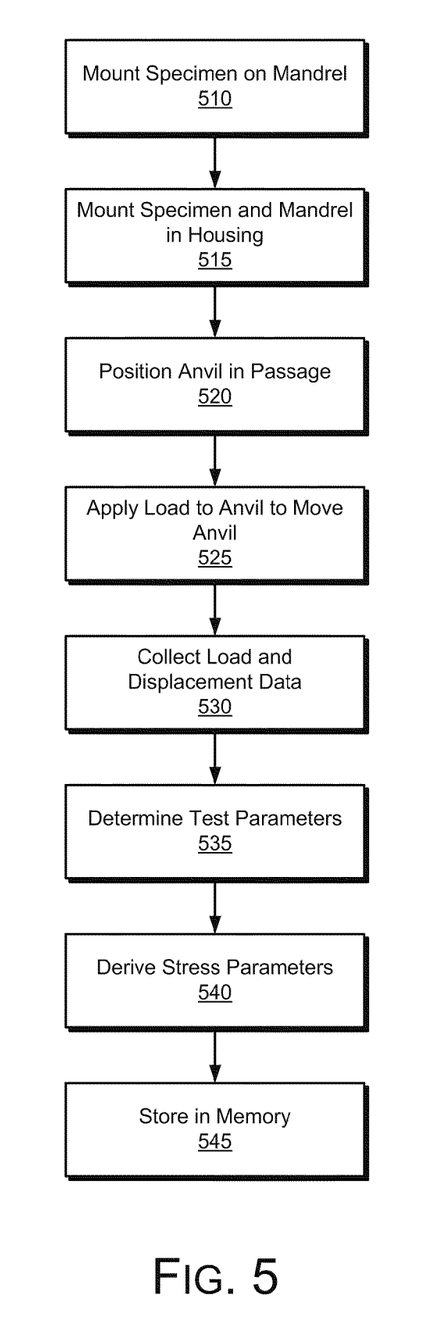
FIG. 5 is a flowchart illustrating operations in a method to test specimens in accordance with some embodiments.

Having described the components of the system 100, a description of methods for using the system 100 will now be provided. FIG. 5 is a flowchart illustrating operations in a method to test specimens in accordance with some embodiments. Referring to FIG. 5, at operation 510 a specimen 140 is mounted on a mandrel 130, e.g., by sliding the specimen 140 over the outside surface of the mandrel 130. At operation 515 the specimen and the mandrel are mounted in the housing. In one embodiment the mandrel 130 may be slid onto the shaft of the anvil until a snug fit is achieved between the shaft 122 and the mandrel 130.

At operation 520 the anvil is positioned in the passage 112 of the housing 110. Referring to FIGS. 1-2, the anvil may be lowered into the passage until the mandrel 130 strikes the block 150. Optionally, a second block 152 may be used to position the specimen 140 during the set up process. As illustrated in FIG. 2, block 152 may be removed during the testing process.

At operation 525 the load system 180 applies a load to the anvil, causing the anvil 120 to move in the direction of the load applied. Since the block 150 restricts the motion of the mandrel, the load induces relative motion between the anvil 120 and the mandrel 130. And because the shaft 122 of the anvil 120 is tapered, the relative motion of the anvil and the shaft 122 causes the mandrel 130 to expand in a circumferential direction, thereby applying a circumferential force to the specimen.

In some embodiments the load system 180 continues to apply a force to the anvil 120 until the specimen fails. During the loading process the data collection module 462 collects (operation 530) data generated by the load gauge 184 and the displacement gauge 186. The data may be stored in a computer readable memory module in memory 430.

At operation 535 the analysis module 464 may determine one or more test parameters associated with the specimen. Exemplary parameters are described with reference to FIG. 6, which is a schematic illustration of test configurations in a system to test specimens in accordance with some embodiments.

Figure 6:
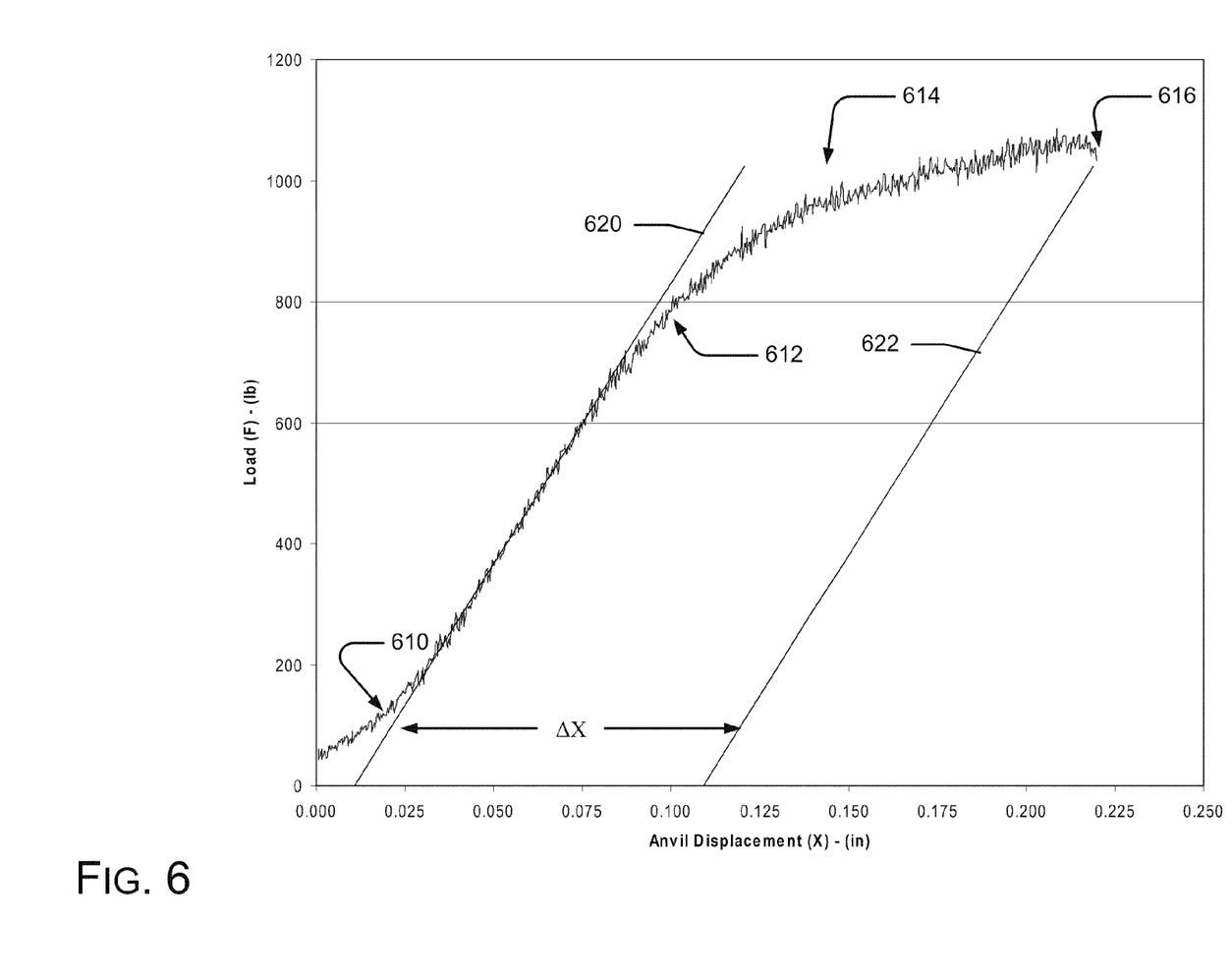
FIG. 6 is a graph illustrating various test parameters associated with a specimen, according to embodiments.

Referring to FIG. 6, in one embodiment the analysis module analyzes the load on the anvil 120 as a function of the displacement of the anvil 120. When plotted on a graph, the data define a stress-strain curve 610 which comprises a section representing an elastic stress region 612, an inelastic strain region, and a point of failure 616. The analysis module 464 may fit a line 620 or curve to approximate the elastic strain section of the curve 610, and a similar line or curve 622 to approximate a strain to failure. The analysis module 464 may also determine the total deformation, $\Delta X$, in the specimen before failure. A variety of stress parameters, e.g., relative strength, ductility, stiffness, and fracture toughness, can be calculated using the test parameters derived from the load data and the deformation data.

Reference in the specification to "one embodiment" or "some embodiments" means that a particular feature, structure, or characteristic described in connection with the embodiment is included in at least an implementation. The appearances of the phrase "in one embodiment" in various places in the specification may or may not be all referring to the same embodiment.

Although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. An apparatus to test a specimen in circumferential tension, comprising:
    a housing defining a passage having a length extending along a longitudinal axis;
    an anvil movable in the passage in a first direction between a first position and a second position along the longitudinal axis, the anvil comprising a tapered shaft section;
    an expandable mandrel having an inner surface adapted to fit around a portion of the tapered shaft section and an outer surface adapted to receive a test specimen; and
    a first block positioned in the housing to limit motion of the mandrel by physically blocking further motion of the mandrel in the first direction;
    wherein moving the anvil between the first position and the second position causes the mandrel to expand in a circumferential direction, thereby applying a circumferential tension force to the specimen.

2. The apparatus of claim 1, wherein the housing comprises a work area formed in the housing.

3. The apparatus of claim 1, wherein the anvil comprises a first section which is substantially cylindrical in shape and a third section which is substantially cylindrical in shape.

4. The apparatus of claim 3, wherein the tapered shaft section of the anvil has a first diameter at a proximal end and a second diameter, less than the first diameter, at a distal end.

5. The apparatus of claim 1, wherein the expandable mandrel comprises an inner surface and an outer surface and varies in thickness along a longitudinal axis, such that the inner surface of the mandrel follows a surface of the tapered shaft while the outer surface of the mandrel maintains a constant radius.

6. The apparatus of claim 5, wherein the mandrel measures between 0.5 inches and 6.0 inches in length along the longitudinal axis.

7. The apparatus of claim 1, further comprising at least one load gauge to measure a load applied to the anvil during operation of the apparatus and a displacement gauge to measure displacement of the anvil along the longitudinal axis during operation of the apparatus.

8. The apparatus of claim 7, further comprising a data collection module to collect load data from the load gauge and displacement data from the displacement gauge during operation of the apparatus and to store the load data and displacement data in a computer readable medium.

9. The apparatus of claim 8, further comprising an analysis module to determine a stress parameter from the load data and the displacement data by plotting the load data against the displacement data to define a stress-strain curve.

10. The apparatus of claim 9, wherein the stress-strain curve comprises a first section representing an elastic stress region, a second section representing an inelastic strain region, and a third region representing a point of failure.

11. A method to test a specimen in circumferential tension, comprising:
    providing a housing defining a passage having a length extending along a longitudinal axis;
    mounting the specimen on the outer surface of an expandable mandrel;
    mounting the expandable mandrel on a tapered shaft section of an anvil;
    positioning a first block in the passage to limit motion of the mandrel in a first direction;
    positioning the anvil in the passage having a length extending along a longitudinal axis; and moving the anvil in the passage between a first position and a second position along the longitudinal axis causes the mandrel to expand, thereby applying a circumferential tension force to the specimen.

12. The method of claim 11, wherein mounting the specimen on the outer surface of an expandable mandrel comprises sliding the specimen over the outer surface of the mandrel.

13. The method of claim 11, wherein the tapered shaft section of the anvil has a first diameter at a proximal end and a second diameter, less than the first diameter, at a distal end, and wherein mounting the expandable mandrel the tapered shaft comprises sliding the mandrel from the distal end of the shaft toward the.

14. The method of claim 11, wherein moving the anvil in the passage between a first position and a second position along the longitudinal axis comprises applying a load to the head of the anvil.

15. The method of claim 14, further comprising:
    collecting load data and displacement data resulting from applying the load to the anvil; and
    determining at least one stress parameter from the load data and the displacement data by plotting the load data against the displacement data to define a stress-strain curve.

16. The method of claim 11, wherein the stress-strain curve comprises a first section representing an elastic stress region, a second section representing an inelastic strain region, and a third region representing a point of failure.

* * * * *